(12) United States Patent
Hötten et al.

(10) Patent No.: US 7,141,239 B2
(45) Date of Patent: ***Nov. 28, 2006

(54) GROWTH/DIFFERENTIATION FACTOR OF THE TGF-β FAMILY

(75) Inventors: Gertrud Hötten, Herne (DE); Helge Neidhardt, Marburg (DE); Rolf Bechtold, Heidelberg (DE); Jens Pohl, Hambruecken (DE)

(73) Assignee: Biopharm Gesellschaft zur Biotechnologischen Entwicklung von Pharmaka mbH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/105,344

(22) Filed: Apr. 14, 2005

(65) Prior Publication Data

US 2005/0175553 A1    Aug. 11, 2005

Related U.S. Application Data

(60) Division of application No. 09/901,556, filed on Sep. 24, 1999, now Pat. No. 7,067,637, which is a division of application No. 08/289,222, filed on Aug. 12, 1994, now Pat. No. 6,120,760, which is a continuation-in-part of application No. PCT/EP93/00350, filed on Feb. 12, 1993.

(30) Foreign Application Priority Data

Feb. 12, 1992   (EP)   .................................. 92102324
Jul. 1, 1994    (DE)   .................................. 44 23 190

(51) Int. Cl.
  *C07K 14/475*   (2006.01)
  *A61K 38/19*    (2006.01)
(52) U.S. Cl. ...................................... 424/85.1; 530/351
(58) Field of Classification Search ............... None
See application file for complete search history.

(56) References Cited

U.S. PATENT DOCUMENTS 4,741,998 A   5/1988   Herr et al.
5,011,912 A   4/1991   Hopp et al.
5,061,786 A   10/1991  Burnier et al.
5,801,014 A   9/1998   Lee et al.
5,807,713 A   9/1998   Hotten et al.
5,994,094 A   11/1999  Hotten et al.
6,120,760 A   9/2000   Hotten et al.
6,171,584 B1  1/2001   Hotten et al.
6,197,550 B1  3/2001   Hotten et al.
6,531,450 B1  3/2003   Hotten et al.
6,764,994 B1  7/2004   Hotten et al.

FOREIGN PATENT DOCUMENTS

EP   0 222 491    5/1987
EP   95/02552     1/1996
WO   WO 93/16099  8/1993

OTHER PUBLICATIONS

Mikayama et al. Proc. Natl. Acad. Sci. USA. vol. 90, pp. 10056-10060.*
Voet et al. Biochemistry. John Wiley & Sons, Inc., pp. 126-128 and 228-234.*
The Journal of Biological Chemistry, Chang et al., vol. 269, No. 45, pp. 28227-28234 (Nov. 11, 1994).
Ganong, Review of Medical Physiology, 17th Edition, 1995, Appleton & Lang, pp. 220, 445.
Creighton, Proteins, Structures and Molecular Principles, 1984, Freeman & Co., pp. 70-73.
Stratagene Catalog, 1988, pp. 39.

* cited by examiner

*Primary Examiner*—Prema Mertz
(74) *Attorney, Agent, or Firm*—Rothwell, Figg, Ernst & Manbeck, P.C.

(57) ABSTRACT

The invention provides DNA sequences encoding novel members of the TGF-β family of proteins. The TGF-β family comprises proteins which function as growth and/or differentiation factors and which are useful in medical applications. Accordingly, the invention also describes the isolation of the above-mentioned DNA sequences, the expression of the encoded proteins, the production of said proteins and pharmaceutical compositions containing said proteins.

3 Claims, 3 Drawing Sheets

Fig.1a

```
              10         20         30         40         50
MP 52   CSRKALHVNF KDMGWDDWII APLEYEAFHC EGLCEFPLRS HLEPTNHAVI

BMP 2   CKRHPLYVDF SDVGWNDWIV APPGYHAFYC HGECPFPLAD HLNSTNHAIV

BMP 4   CRRHSLYVDF SDVGWNDWIV APPGYQAFYC HGDCPFPLAD HLNSTNHAIV

BMP 5   CKKHELYVSF RDLGWQDWII APEGYAAFYC DGECSFPLNA HMNATNHAIV

BMP 6   CRKHELYVSF QDLGWQDWII APKGYAANYC DGECSFPLNA HMNATNHAIV

BMP 7   CKKHELYVSF RDLGWQDWII APEGYAAYYC EGECAFPLNS YMNATNHAIV
        * +  * * *  * ** ***+  **  * *+ *  +* * *** +  ++ ****

60         70         80         90        100
MP 52   QTLMNSMDPE STPPTCCVPT RLSPISILFI DSANNVVYKQ YEDMVVESCG CR

BMP 2   QTLVNSVNS- KIPKACCVPT ELSAISMLYL DENEKVVLKN YQDMVVEGCG CR

BMP 4   QTLVNSVNS- SIPKACCVPT ELSAISMLYL DEYDKVVLKN YQEMVVEGCG CR

BMP 5   QTLVHLMFPD HVPKPCCAPT KLNAISVLYF DDSSNVILKK YRNMVVRSCG CH

BMP 6   QTLVHLMNPE YVPKPCCAPT KLNAISVLYF DDNSNVILKK YRNMVVRACG CH

BMP 7   QTLVHFINPE TVPKPCCAPT QLNAISVLYF DDSSNVILKK YRNMVVRACG CH
        *** +++ ++  + *  **+**  *+ ** *    *  +*+ *   * +***++**  *+
```

Fig. 1b

```
                    10              20              30          40
MP121    C C R Q E F F V D F   R E I G W H D W I I   Q P E G Y A M N F C   I G Q C P L H I A G
InhibβA  C C K K Q F F V S F   K D I G W N D W I I   A P S G Y H A N Y C   E G E C P S H I A G
InhibβB  C C R Q Q F F I D F   R L I G W N D W I I   A P T G Y Y G N Y C   E G S C P A Y L A G
Inhibα   C H R V A L N I S F   Q E L G W E R W I V   Y P P S F I F H Y C   H G G C G L H I P -
               + +   *         + +   *   * *         +       +   *         +       +   + + +

50              60              70          80
MP121    M P G I A A S F H T   A V L N L L K A N T   A A G T T G G G S C   C - - V P T A R R P
InhibβA  T S G S S L S F H S   T V I N H Y R M R G   H S P F A N L K S C   C - - V P T K L R P
InhibβB  V P G S A S S F H T   A V V N Q Y R M R G   L N P - G T V N S C   C - - I P T K L S T
Inhibα   - - - P N L S L P V   P G A P P T P A Q P   Y S L L P G A Q P C   C A A L P G T M R P
             *       + +       +   + +   +         +         +     * *       * +     +   + +

90             100             110
MP121    L S L L Y Y D R D S   N I V K T D - I P D   M V V E A C G C S
InhibβA  M S M L Y Y D D G Q   N I I K K D - I Q N   M I V E E C G C S
InhibβB  M S M L Y F D D E Y   N I V K R D - V P N   M I V E E C G C A
Inhibα   L H V R T T S D G G   Y S F K Y E T V P N   L L T Q H C A C I
           +       +           + +   +       +       +     * +   * +
```

Fig.2a

```
             Eco RI Nco I
OD           ATGAATTCCCATGGACCTGGGCTGGMAKGAMTGGAT
BMP 2                        ACGTGGGGTGGAATGACTGGAT
BMP 3                        ATATTGGCTGGAGTGAATGGAT
BMP 4                        ATGTGGGCTGGAATGACTGGAT
BMP 7                        ACCTGGGCTGGCAGGACTGGAT
TGF-β1                       AGGACCTCGGCTGGAAGTGGAT
TGF-β2                       GGGATCTAGGGTGGAAATGGAT
TGF-β3                       AGGATCTGGGCTGGAAGTGGGT
Inhibin α                    AGCTGGGCTGGGAACGGTGGAT
Inhibin βA                   ACATCGGCTGGAATGACTGGAT
Inhibin βB                   TCATCGGCTGGAACGACTGGAT
```

Fig.2b

```
             Eco RI
OID          ATGAATTCGAGCTGCGTSGGSRCACAGCA
BMP 2                    GAGTTCTGTCGGGACACAGCA
BMP 3                    CATCTTTTCTGGTACACAGCA
BMP 4                    CAGTTCAGTGGGCACACAACA
BMP 7                    GAGCTGCGTGGGCGCACAGCA
TGF-β1                   CAGCGCCTGCGGCACGCAGCA
TGF-β2                   TAAATCTTGGGACACGCAGCA
TGF-β3                   CAGGTCCTGGGGCACGCAGCA
inhibin α                CCCTGGGAGAGCAGCACAGCA
inhibin βA               CAGCTTGGTGGGCACACAGCA
inhibin βB               CAGCTTGGTGGGAATGCAGCA
```

GROWTH/DIFFERENTIATION FACTOR OF THE TGF-β FAMILY

CROSS REFERENCE TO RELATED APPLICATION

This application is a Divisional of Ser. No. 09/901,556 filed Sep. 24, 1999 now U.S. Pat. No. 7,067,637; which is a Divisional of Ser. No. 08/289,222 filed Aug. 12, 1994, now U.S. Pat. No. 6,120,760; which is a CIP of PCT/EP93/00350 filed Feb. 12, 1993.

The present invention relates to DNA sequences encoding novel growth/differentiation factors of the TGF-β family. In particular, it relates to novel DNA sequences encoding TGF-β-like proteins, to the isolation of said DNA sequences, to expression plasmids containing said DNA, to microorganisms transformed by said expression plasmid, to the production of said protein by culturing said transformant, and to pharmaceutical compositions containing said protein. The TGF-β family of growth factors comprising BMP, TGF, and Inhibin related proteins (Roberts and Sporn, Handbook of Experimental Pharmacology 95 (1990), 419–472) is of particular relevance in a wide range of medical treatments and applications. These factors are useful in processes relating to wound healing and tissue repair. Furthermore, several members of the TGF-β family are tissue inductive, especially osteo-inductive, and consequently play a crucial role in inducing cartilage and bone development.

Wozney, Progress in Growth Factor Research 1 (1989), 267–280 and Vale et al., Handbook of Experimental Pharmacology 95 (1990), 211–248 describe different growth factors such as those relating to the BMP (bone morphogenetic proteins) and the Inhibin group. The members of these groups share significant structural similarity. The precursor of the protein is composed of an aminoterminal signal sequence, a propeptide and a carboxyterminal sequence of about 110 amino acids, which is subsequently cleaved from the precursor and represents the mature protein. Furthermore, their members are defined by virtue of amino acid sequence homology. The mature protein contains the most conserved sequences, especially seven cysteine residues which are conserved among the family members. The TGF-β-like proteins are multifunctional, hormonally active growth factors. They also share related biological activities such as chemotactic attraction of cells, promoting cell differentiation and their tissue-inducing capacity, such as cartilage- and bone-inducing capacity. U.S. Pat. No. 5,013,649 discloses DNA sequences encoding osteo-inductive proteins termed BMP-2 proteins (bone morphogenetic protein), and U.S. patent applications Ser. Nos. 179,101 and 179,197 disclose the BMP proteins BMP-1 and BMP-3. Furthermore, many cell types are able to synthesize TGF-β-like proteins and virtually all cells possess TGF-β receptors.

Taken together, these proteins show differences in their structure, leading to considerable variation in their detailed biological function. Furthermore, they are found in a wide variety of different tissues and developmental stages. Consequently, they might possess differences concerning their function in detail, for instance the required cellular physiological environment, their lifespan, their targets, their requirement for accessory factors, and their resistance to degradation. Thus, although numerous proteins exhibiting tissue-inductive, especially osteo-inductive potential are described, their natural role in the organism and, more importantly, their medical relevance must still be elucidated in detail. The occurrence of still-unknown members of the TGF-β family relevant for osteogenesis or differentiation/induction of other tissues is strongly suspected. However, a major problem in the isolation of these new TGF-β-like proteins is that their functions cannot yet be described precisely enough for the design of a discriminative bioassay. On the other hand, the expected nucleotide sequence homology to known members of the family would be too low to allow for screening by classical nucleic acid hybridization techniques. Nevertheless, the further isolation and characterization of new TGF-β-like proteins is urgently needed in order to get hold of the whole set of induction and differentiation proteins meeting all desired medical requirements. These factors might find useful medical applications in defect healing and treatments of degenerative disorders of bone and/or other tissues like, for example, kidney and liver.

Thus, the technical problem underlying the present invention essentially is to provide DNA sequences coding for new members of the TGF-β protein family having mitogenic and/or differentiation-inductive, e.g. osteo-inductive potential.

The solution to the above technical problem is achieved by providing the embodiments characterized in claims 1 to 17. Other features and advantages of the invention will be apparent from the description of the preferred embodiments and the drawings. The sequence listings and drawings will now briefly be described.

SEQ ID NO. 1 shows the nucleotide sequence of MP-52, i.e. the embryo derived sequence corresponding to the mature peptide and most of the sequence coding for the propeptide of MP-52.

Some of the propeptide sequence at the 5'-end of MP-52 has not been characterized so far.

SEQ ID NO. 2 shows the nucleotide sequence of MP-121, i.e. the liver derived sequence corresponding to the mature peptide, the sequence coding for the propeptide of MP-121, and sequences 5' and 3' to the coding region.

The start codon begins with nucleotide 128 of SEQ ID NO.2. The sequence coding for the mature MP121 polypeptide begins with nucleotide 836 of SEQ ID NO. 2. The stop codon begins with nucleotide 1184 of SEQ ID NO. 2. The sequence coding for the precursor protein has a length of 1056 bp. The sequence coding for the propeptide has a length of 708 bp and the sequence coding for the mature peptide has a length of 348 bp.

SEQ ID NO. 3 shows the amino acid sequence of MP-52 as deduced from SEQ ID NO. 1.

SEQ ID NO. 4 shows the amino acid sequence of MP-121 as deduced from sequence SEQ ID NO.2. The sequence of the mature polypeptide begins with amino acid 237 of SEQ ID NO. 4. The precursor protein has a length of 352 amino acids. The propeptide and the mature peptide have a length of 236 and 116 amino acids, respectively.

SEQ ID NO. 5 shows a part of the nucleotide sequence of the liver derived sequence of MP-121.

SEQ ID NO. 6 shows a part of the nucleotide sequence of the embryo derived sequence of MP-52.

The shorter DNA-sequences SEQ ID NO. 5 and 6 can be useful for example for isolation of further members of the TGF-β-protein family.

FIG. 1 shows an alignment of the amino acid sequences of MP-52 and MP-121 starting from the first of the seven conserved cysteines with some related proteins. Ia shows the alignment of MP-52 with some members of the BMP protein family (SEQ ID NOS: 22–27); Ib shows the alignment of MP-121 with some members of the Inhibin protein family SEQ ID NOS: 28–31). * indicates that the amino acid is the same in all proteins compared; +indicates that the amino acid is the same in at least one of the proteins compared with MP-52 (FIG. Ia) or MP-121 (FIG. Ib).

FIG. 2 shows the nucleotide sequences of the oligonucleotide primer as used in the present invention and an alignment of these sequences with known members of the TGF-β family (SEQ ID NOS: 32–53). M means A or C; S means C or G; R means A or G; and K means G or T. 2a depicts the sequence of the primer OD (SEQ ID NOS: 32); 2b shows the sequence of the primer OID (SEQ ID NOS: 42).

The present invention relates to novel TGF-β-like proteins and provides DNA sequences contained in the corresponding genes. Such sequences include nucleotide sequences comprising the sequence

```
                           (SEQ ID NO:7)
    ATGAACTCCATGGACCCCGAGTCCACA and (SEQ ID NO:8)
    CTTCTCAAGGCCAACACAGCTGCAGGCACC
``` and in particular sequences as illustrated in SEQ ID Nos. 1 and 2, allelic derivatives of said sequences and DNA sequences degenerated as a result of the genetic code for said sequences. They also include DNA sequences hybridizing under stringent conditions with the DNA sequences mentioned above and containing the following amino acid sequences:

```
                           (SEQ ID NO:9)
    Met-Asn-Ser-Met-Asp-Pro-Glu-Ser-Thr or (SEQ ID NO:10)
    Leu-Leu-Lys-Ala-Asn-Thr-Ala-Ala-Gly-Thr.
```

Although said allelic, degenerate and hybridizing sequences may have structural divergencies due to naturally occurring mutations, such as small deletions or substitutions, they will usually still exhibit essentially the same useful properties, allowing their use in basically the same medical applications.

According to the present invention, the term "hybridization" means conventional hybridization conditions, preferably conditions with a salt concentration of 6×SSC at 62° to 66° C. followed by a one-hour wash with 0.6×SSC, 0.1% SDS at 62° to 66° C. The term "hybridization" preferably refers to stringent hybridization conditions with a salt concentration of 4×SSC at 62°–66° C. followed by a one-hour wash with 0.1×SSC, 0.1% SDS at 62°–66° C.

Important biological activities of the encoded proteins, preferably MP-52, comprise a mitogenic and osteo-inductive potential and can be determined in assays according to Seyedin et al., PNAS 82 (1985), 2267–2271 or Sampath and Reddi, PNAS 78 (1981), 7599–7603.

The biological properties of the proteins according to the invention, preferably MP-121, may be determined, e.g., by means of the assays according to Wrana et al. (Cell 71, 1003–1014 (1992)), Ling et al. (Proc. Natl. Acad. of Science, 82, 7217–7221 (1985)), Takuwa et al. (Am. J. Physiol., 257, E797–E803 (1989)), Fann and Patterson (Proc. Natl. Acad. of Science, 91, 43–47 (1994)), Broxmeyer et al. (Proc. Natl. Acad. of Science, 85, 9052–9056 (1988)), Green et al. (Cell, 71, 731–739 (1992)), Partridge et al. (Endocrinology, 108, 213–219 (1981)) or Roberts et al. (PNAS 78, 5339–5343 (1981)).

Preferred embodiments of the present invention are DNA sequences as defined above and obtainable from vertebrates, preferably mammals such as pig or cow and from rodents such as rat or mouse, and in particular from primates such as humans.

Particularly preferred embodiments of the present invention are the DNA sequences termed MP-52 and MP-121 which are shown in SEQ ID Nos. 1 and 2. The corresponding transcripts of MP-52 were obtained from embryogenic tissue and code for a protein showing considerable amino acid homology to the mature part of the BMP-like proteins (see FIG. 1a). The protein sequences of BMP2 (=BMP2A) and BMP4 (=BMP2B) are described in Wozney et al., Science Vol 242, 1528–1534 (1988). The respective sequences of BMP5, BMP6 and BMP7 are described in Celeste et al., Proc. Natl. Acad. Sci. USA Vol 87, 9843–9847 (1990). Some typical sequence homologies, which are specific to known BMP-sequences only, were also found in the propeptide part of MP-52, whereas other parts of the precursor part of MP-52 show marked differences to BMP-precursors. The mRNA of MP-121 was detected in liver tissue, and its corresponding amino acid sequence shows homology to the amino acid sequences of the Inhibin protein chains (see FIG. 1b). cDNA sequences encoding TGF-β-like proteins have not yet been isolated from liver tissue, probably due to a low abundance of TGF-β specific transcripts in this tissue. In embryogenic tissue, however, sequences encoding known TGF-β-like proteins can be found in relative abundance. The inventors have recently detected the presence of a collection of TGF-β-like proteins in liver as well. The high background level of Clones related to known factors of this group presents the main difficulty in establishing novel TGF-β-related sequences from these and probably other tissues. In the present invention, the cloning was carried out according to the method described below. Once the DNA sequence has been cloned, the preparation of host cells capable of producing the TGF-β-like proteins and the production of said proteins can be easily accomplished using known recombinant DNA techniques comprising constructing the expression plasmids encoding said protein and transforming a host cell with said expression plasmid, cultivating the transformant in a suitable culture medium, and recovering the product having TGF-β-like activity.

Thus, the invention also relates to recombinant molecules comprising DNA sequences as described above, optionally linked to an expression control sequence. Such vectors may be useful in the production of TGF-β-like proteins in stably or transiently transformed cells. Several animal, plant, fungal and bacterial systems may be employed for the transformation and subsequent cultivation process. Preferably, expression vectors which can be used in the invention contain sequences necessary for the replication in the host cell and are autonomously replicable. It is also preferable to use vectors containing selectable marker genes which can be easily selected for transformed cells. The necessary operation is well-known to those skilled in the art.

It is another object of the invention to provide a host cell transformed by an expression plasmid of the invention and capable of producing a protein of the TGF-β family. Examples of suitable host cells include various eukaryotic and prokaryotic cells, such as E. coli, insect cells, plant cells, mammalian cells, and fungi such as yeast.

Another object of the present invention is to provide a protein of the TGF-β family encoded by the DNA sequences described above and displaying biological features such as tissue-inductive, in particular osteo-inductive and/or mitogenic capacities possibly relevant to therapeutical treatments. The above-mentioned features of the protein might vary depending upon the formation of homodimers or heterodimers. Such structures may prove useful in clinical applications as well. The amino acid sequence of the especially preferred proteins of the TGF-β-family (MP-52 and MP-121) are shown in SEQ ID NO. 3 and SEQ ID NO. 4.

It is a further aspect of the invention to provide a process for the production of TGF-β-like proteins. Such a process comprises cultivating a host cell being transformed with a DNA sequence of the present invention in a suitable culture medium and purifying the TGF-β-like protein produced. Thus, this process will allow the production of a sufficient amount of the desired protein for use in medical treatments or in applications using cell culture techniques requiring growth factors for their performance. The host cell is obtainable from bacteria such as *Bacillus* or *Escherichia coli*, from fungi such as yeast, from plants such as tobacco, potato, or *Arabidopsis*, and from animals, in particular vertebrate cell lines such as the Mo-, COS- or CHO cell line.

Yet another aspect of the present invention is to provide a particularly sensitive process for the isolation of DNA sequences corresponding to low abundance mRNAs in the tissues of interest. The process of the invention comprises the combination of four different steps. First, the mRNA has to be isolated and used in an amplification reaction using oligonucleotide primers. The sequence of the oligonucleotide primers contains degenerated DNA sequences derived from the amino acid sequence of proteins related to the gene of interest. This step may lead to the amplification of already known members of the gene family of interest, and these undesired sequences would therefore have to be eliminated. This object is achieved by using restriction endonucleases which are known to digest the already-analyzed members of the gene family. After treatment of the amplified DNA population with said restriction endonucleases, the remaining desired DNA sequences are isolated by gel electrophoresis and reamplified in a third step by an amplification reaction, and in a fourth step they are cloned into suitable vectors for sequencing. To increase the sensitivity and efficiency, steps two and three are repeatedly performed, at least two times in one embodiment of this process.

In a preferred embodiment, the isolation process described above is used for the isolation of DNA sequences from liver tissue. In a particularly preferred embodiment of the above-described process, one primer used for the PCR experiment is homologous to the polyA tail of the mRNA, whereas the second primer contains a gene-specific sequence. The techniques employed in carrying out the different steps of this process (such as amplification reactions or sequencing techniques) are known to the person skilled in the art and described, for instance, in Sambrook et al., 1989, "Molecular Cloning: A laboratory manual", Cold Spring Harbor Laboratory Press.

It is another object of the present invention to provide pharmaceutical compositions containing a therapeutically-effective amount of a protein of the TGF-β family of the present invention. Optionally, such a composition comprises a pharmaceutically acceptable carrier. Such a therapeutic composition can be used in wound healing and tissue repair as well as in the healing of bone, cartilage, or tooth defects, either individually or in conjunction with suitable carriers, and possibly with other related proteins or growth factors. Thus, a therapeutic composition of the invention may include, but is not limited to, the MP-52 encoded protein in conjunction with the MP-121 encoded protein, and optionally with other known biologically-active substances such as EGF (epidermal growth factor) or PDGF (platelet derived growth factor). Another possible clinical application of a TGF-β-like protein is the use as a suppressor of the immuno response, which would prevent rejection of organ transplants. The pharmaceutical composition comprising the proteins of the invention can also be used prophylactically, or can be employed in cosmetic plastic surgery. Furthermore, the application of the composition is not limited to humans but can include animals, in particular domestic animals, as well. Possible applications of the pharmaceutical composition according to the invention include furthermore treatment or prevention of connective tissue, skin, mucous membrane, endothelial, epithelial, neuronal or renal defects, use in the case of dental implants, use as a morphogenic factor used for inducing liver tissue growth, induction of the proliferation of precursor cells or bone marrow cells, for maintaining a differentiated state and the treatment of impaired fertility or for contraception.

Finally, another object of the present invention is an antibody or antibody fragment, which is capable of specifically binding to the proteins of the present invention. Methods to raise such specific antibody are general knowledge. Preferably such an antibody is a monoclonal antibody. Such antibodies or antibody fragments might be useful for diagnostic methods.

The following examples illustrate in detail the invention disclosed, but should not be construed as limiting the invention.

EXAMPLE 1

Isolation of MP-121

1.1 Total RNA was isolated from human liver tissue (40-year-old-male) by the method of Chirgwin et al., Biochemistry 18 (1979), 5294–5299. Poly $A^+$ RNA was separated from total RNA by oligo (dT) chromatography according to the instructions of the manufacturer (Stratagene Poly (A) Quick columns).

1.2 For the reverse transcription reaction, poly $A^+$ RNA (1–2.5 μg) derived from liver tissue was heated for 5 minutes to 65° C. and cooled rapidly on ice. The reverse transcription reagents containing 27 U RNA guard (Pharmacia), 2.5 μg oligo $d(T)_{12-18}$ (Pharmacia) 5×buffer (250 mM Tris/HCl pH 8.5; 50 mM $MgCl_2$; 50 mM DTT; 5 mM each dNTP; 600 mM KCl) and 20 units avian myeloblastosis virus reverse transcriptase (AMV, Boehringer Mannheim) per μg poly ($A^+$) RNA were added. The reaction mixture (25 μl) was incubated for 2 hours at 42° C. The liver cDNA pool was stored at −20° C.

1.3 The deoxynucleotide primers OD and OID (FIG. 2) designed to prime the amplification reaction were generated on an automated DNA-synthesizer (Biosearch). Purification was done by denaturating polyacrylamide gel electrophoresis and isolation of the main band from the gel by isotachophoresis. The oligonucleotides were designed by aligning the nucleic acid sequences of some known members of the TGF-β family and selecting regions of the highest conservation. An alignment of this region is shown in FIG. 2. In order to facilitate cloning, both oligonucleotides contained EcoR I restriction sites and OD additionally contained an Nco I restriction site at its 5' terminus.

1.4 In the polymerase chain reaction, a liver-derived cDNA pool was used as a template in a 50 μl reaction mixture. The amplification was performed in 1×PCR-buffer (16.6 mM $(NH_4)_2SO_4$; 67 mM Tris/HCl pH 8.8; 2 mM $MgCl_2$; 6.7 μM EDTA; 10 mM β-mercaptoethanol; 170 μg/ml BSA (Gibco)), 200 μM each dNTP (Pharmacia), 30 pmol each oligonucleotide (OD and OID) and 1.5 units Taq polymerase (AmpliTaq, Perkin Elmer Cetus). The PCR reaction contained cDNA corresponding to 30 ng of poly (A⁺) RNA as staring material. The reaction mixture was overlayed by paraffine and 40 cycles (cycle 1: 80 s 93° C./40s 52° C./40s 72° C.; cycles 2–9: 60s 93° C./40s 52° C./40s 72° C.; cycles 10–29: 60s 93° C./40s 52° C./60s 72° C.; cycles 30–31: 60s 93° C./40s 52° C./90s 72° C.; cycle 40: 60s 93° C./40s 52° C./420s 72° C.) of the PCR were performed. Six PCR-reaction mixtures were pooled, purified by subsequent extractions with equal volumes of phenol, phenol/chloroform (1:1 (v/v)) and chloroform/isoamylalcohol (24:1 (v/v)) and concentrated by ethanol precipitation.

1.5 One half of the obtained PCR pool was sufficient for digestion with the restriction enzymes Sph I (Pharmacia) and AlwN I (Biolabs). The second half was digested in a series of reactions by the restriction enzymes Ava I (BRL), AlwN I (Biolabs) and Tfi I (Biolabs). The restriction endonuclease digestions were performed in 100 μl at 37° C. (except Tfi I at 65° C.) using 8 units of each enzyme in a 2- to 12-hour reaction in a buffer recommended by the manufacturer.

1.6 Each DNA sample was fractioned by electrophoresis using a 4% agarose gel (3% FMC Nusieve agarose, Biozym and 1% agarose, BRL) in Tris borate buffer (89 mM Trisbase, 89 mM boric acid, 2 mM EDTA, pH 8). After ethidiumbromide staining uncleaved amplification products (about 200 bp; size marker was run in parallel) were excised from the gel and isolated by phenol extraction: an equal volume of phenols was added to the excised agarose, which was minced to small pieces, frozen for 10 minutes, vortexed and centrifuged. The aqueous phase was collected, the interphase reextracted by the same volume TE-buffer, centrifuged and both aqueous phases were combined. DNA was further purified twice by phenol/chloroform and once by chloroform/isoamylalcohol extraction.

1.7 After ethanol precipitation, one fourth or one fifth of the isolated DNA was reamplified using the same 52° C./60s 72° C.; cycle 13: 60s 93° C./40s 52° C./420s 72° C.). The reamplification products were purified, restricted with the same enzymes as above and the uncleaved products were isolated from agarose gels as mentioned above for the amplification products. The reamplification followed by restriction and gel isolation was repeated once.

1.8 After the last isolation from the gel, the amplification products were digested by 4 units EcoR I (Pharmacia) for 0.2 hours at 37° C. using the buffer recommended by the manufacturer. One fourth of the restriction mixture was ligated to the vector pBluescriptII SK+ (Stratagene) which was digested likewise by EcoR I. After ligation, 24 clones from each enzyme combination were further analyzed by sequence analysis. The sample restricted by AlwN I and Sph I contained no new sequences, only BMP6 and Inhibin βA sequences. 19 identical new sequences, which were named MP-121, were found by the Ava I, AlwN I and Tfi I restricted samples. The MP-121 containing plasmids were called pSK MP-121 (OD/OID). One sequence differed from this mainly-found sequence by two nucleotide exchanges. Ligation reaction and transformation in E. coli HB101 were performed as described in Sambrook et al., Molecular cloning: A laboratory manual (1989). Transformants were selected by Ampicillin resistance and the plasmid DNAs were isolated according to standard protocols (Sambrook et al. (1989)).

Analysis was done by sequencing the double-stranded plasmids by "dideoxyribonucleotide chain termination sequencing" with the sequencing kit "Sequenase Version 2.0" (United States Biochemical Corporation).

The clone was completed to the 3' end of the c-DNA by a method described in detail by Frohman (Amplifications, published by Perkin-Elmer Corporation, issue 5 (1990), pp 11–15). The same liver mRNA which was used for the isolation of the first fragment of MP-121 was reverse transcribed using a primer consisting of oligo dT (16 residues) linked to an adaptor primer (AGAATTCGCATGC-CATGGTCGACGAAGC(T)$_{16}$; (SEQ ID NO:11)). Amplification was performed using the adaptor primer (AGAATTCGCATGCCATGGTCGACG (SEQ ID NO:12)) and an internal primer (GGCTACGCCATGAACTTCTG-CATA (SEQ ID NO:13) of the MP-121 sequence. The amplification products were reamplified using a nested internal primer (ACATAGCAGGCATGCCTGGTATTG (SEQ ID NO:14)) of the MP-121 sequence and the adaptor primer. The reamplification products were cloned after restriction with Sph I in the likewise restricted vector pT7/T3 U19 (Pharmacia) and sequenced with the sequencing kit "Sequenase Version 2.0" (United States Biochemical Corporation). Clones were characterized by their sequence overlap to the 3' end of the known MP-121 sequence.

One clone, called p121Lt 3' MP13, was used to isolate a NcoI (blunt ended with T$_4$ polymerase)/SphI fragment. This fragment was ligated into a pSK MP-121 (OD/OID) vector, where the OD primer sequence was located close to the T7 primer sequence of the pSK+ multiple cloning site, opened with SphI/SmaI. The resulting plasmid was called pMP121DFus6. It contains MP-121 specific sequence information starting from position 922 and ending with position 1360 of SEQ ID NO. 2.

1.9 Using a DdeI fragment of pMP-121DFus6 as a probe, ranging from nucleotide 931 to nucleotide 1304 of SEQ ID NO. 2, a human liver cDNA library (Clontech, # HL3006b, Lot 36223) was screened by a common method described in detail by Ausubel et al. (Current Protocols in Molecular Biology, published by Greene Publishing Associates and Wiley-Interscience (1989)). From $8.1 \times 10^5$ phages, 24 mixed clones were isolated and re-screened using the DdeI fragment. 10 clones were confirmed and the EcoRI fragments subcloned into Bluescript SK (Stratagene, #212206). EcoRI restriction analysis showed that one clone (SK121 L9.1, deposited by the DSM (#9177) has an insert of about 2.3 kb. This clone contains the complete reading frame of the MP121 gene and further information to the 5' and 3' end in addition to the sequence isolated from mRNA by the described amplification methods. The complete sequence of the EcoRI insert of SK121 L9.1 is shown in SEQ ID NO.2. The reading frame of the MP-121 gene could be confirmed by sequencing of another clone (SK121 L11.1), having the identical reading frame sequence as SK121 L9.1. The beginning of the start codon of the MP-121 sequence of SK121 L9.1 could be determined at position 128 of SEQ ID NO.2, since there are three stop codons in-frame in front of the start codon at positions 62, 77 and 92. The start site of the mature MP-121 is at position 836 of SEQ ID NO.2 in sequence analogy to other members of the TGF-β-family, corresponding to amino acid 237 in SEQ ID NO.4. The stop codon is at position 1184 of SEQ ID NO.2.

Plasmid SK121 L9.1 was deposited under number 9177 at DSM (Deutsche Sammlung von Mikroorganismen und Zellkulturen), Mascheroder Weg 1b, Braunschweig, on 26.04.94).

EXAMPLE 2

Isolation of MP-52

A further cDNA sequence, MP-52, was isolated according to the above described method (Example 1) by using RNA from human embryo (8–9 weeks old) tissue. The PCR reaction contained cDNA corresponding to 20 ng of poly (A$^+$)RNA as starting material. The reamplification step was repeated twice for both enzyme combinations. After ligation, 24 clones from each enzyme combination were further analyzed by sequence analysis. The sample restricted by AlwN I and Sph I yielded a new sequence which was named MP-52. The other clones comprised mainly BMP6 and one BMP7 sequence. The sample restricted by Ava I, AlwN I and Tfi I contained no new sequences, but consisted mainly of BMP7 and a few Inhibin βA sequences.

The clone was completed to the 3' end according to the above described method (Example 1). The same embryo mRNA, which was used for the isolation of the first fragment of MP-52, was reverse transcribed as in Example 1. Amplification was performed using the adaptor primer (AGAATTCGCATGCCATGGTCGACG (SEQ ID NO:12)) and an internal primer (CTTGAGTACGAGGCTTTC-CACTG (SEQ ID NO: 15)) of the MP-52 sequence. The amplification products were reamplified using a nested adaptor primer (ATTCGCATGCCATGGTCGACGAAG (SEQ ID NO: 16)) and a nested internal primer (GGAGCCCAC-GAATCATGCAGTCA (SEQ ID NO:17)) of the MP-52 sequence. The reamplification products were cloned after restriction with Nco I in a likewise restricted vector (pUC 19 (Pharmacia #27-4951 -01) with an altered multiple cloning site containing a unique Nco I restriction site) and sequenced. Clones were characterized by their sequence overlap to the 3' end of the known MP-52 sequence. Some of these clones contain the last 143 basepairs of the 3' end of the sequence shown in SEQ ID NO: 1 and the 0.56 kb 3' non translated region (sequence not shown). One of these was used as a probe to screen a human genomic library (Stratagene #946203) by a common method described in detail by Ausubel et at. (Current Protocols in Molecular Biology, published by Greene publishing Associates and Wiley-Interscience (1989)). From 8×10$^5$ λ phages one phage (λ 2.7.4) which was proved to contain an insert of about 20 kb, was isolated and deposited by the DSM (#7387). This clone contains in addition to the sequence isolated from mRNA by the described amplification methods sequence information further to the 5' end. For sequence analysis a Hind III fragment of about 7,5 kb was subcloned in a likewise restricted vector (Bluescript SK, Stratagene #212206). This plasmid, called SKL 52 (H3) MP12, was also deposited by the DSM (#7353). Sequence information derived from this clone is shown in SEQ ID NO: 1. At nucleotide No. 1050, the determined cDNA and the respective genomic sequence differ by one basepair (cDNA: G; genomic DNA: A). We assume the genomic sequence to be correct, as it was confirmed also by sequencing of the amplified genomic DNA from embryonic tissue which had been used for the mRNA preparation. The genomic DNA contains an intron of about 2 kb between basepairs 332 and 333 of SEQ ID NO: 1. The sequence of the intron is not shown. The correct exon/exon junction was confirmed by sequencing an amplification product derived from cDNA which comprises this region. This sequencing information was obtained by the help of a slightly modified method described in detail by Frohman (Amplifications, published by Perkin-Elmer Corporation, issue 5 (1990), pp 11–15). The same embryo RNA which was used for the isolation of the 3' end of MP-52 was reverse transcribed using an internal primer of the MP-52 sequence oriented in the 5' direction (ACAGCAGGTGGGTGGTGTGGACT (SEQ ID NO: 18)). A polyA tail was appended to the 5' end of the first strand cDNA by using terminal transferase. A two step amplification was performed first by application of a primer consisting of oligo dT and an adaptor primer (AGAATTCGCAT-GCCATGGTCGACGAAGC(T$_{16}$)(SEQ ID NO:11)) and secondly an adaptor primer (AGAATTCGCATGCCATG-GTCGACG (SEQ ID NO: 12)) and an internal primer (CCAGCAGCCCATCCTTCTCC (SEQ ID NO: 19)) of the MP-52 sequence. The amplification products were reamplified using the same adaptor primer and a nested internal primer (TCCAGGGCACTAATGTCAAACACG (SEQ ID NO: 20)) of the MP-52 sequence. Consecutively the reamplification products were again reamplified using a nested adaptor primer (ATTCGCATGCCATGGTCGACGAAG (SEQ ID NO: 16)) and a nested internal primer (ACTAAT-GTCAAACACGTACCTCTG (SEQ ID NO: 21)) of the MP-52 sequence. The final reamplification products were blunt end cloned in a vector (Bluescript SK, Stratagene #212206) restricted with EcoRV. Clones were characterized by their sequence overlap to the DNA of λ2.7.4.

Plasmid SKL 52 (H3) MP12 was deposited under number 7353 at DSM (Deutsche Sammlung von Mikroorganismen und Zellkulturen), Mascheroder Weg 1b, 3300 Braunschweig, on 10.12.1992.

Phage λ 2.7.4. was deposited under number 7387 at DSM on 13.1.1993.

The invention claimed is:

1. An isolated protein of the TFG-β-family selected from the group consisting of:
   (a) a protein comprising the amino acid sequence shown in SEQ ID NO:22, wherein said protein has essentially the same cartilage or bone inducing activities as a mature protein encoded by the nucleotide sequence of SEQ ID NO:1, and
   (b) a protein consisting of a fragment of the amino acid sequence of SEQ ID NO:3, wherein said fragment comprises the amino acid sequence shown in SEQ ID NO:22.

2. A pharmaceutical composition comprising a at least one protein according to claim 1 and a pharmaceutically acceptable excipient.

3. The pharmaceutical composition according to claim 2 further comprising a growth/differentiation factor selected from the group consisting of MP-121, epidermal growth factor and platelet derived growth factor.

* * * * *

SEQUENCE LISTING

```
<160> NUMBER OF SEQ ID NOS: 53

<210> SEQ ID NO 1
<211> LENGTH: 1207
<212> TYPE: DNA
<213> ORGANISM: Homo sapiens

<400> SEQUENCE: 1
accgggcggc cctgaaccca agccaggaca ccctccccaa acaaggcagg ctacagcccg      60
gactgtgacc ccaaaaggac agcttcccgg aggcaaggca cccccaaaag caggatctgt     120
ccccagctcc ttcctgctga agaaggccag ggagcccggg cccccacgag agcccaagga    180
```

-continued

| | | |
|---|---|---|
| gccgtttcgc ccacccccca tcacaccccca cgagtacatg ctctcgctgt acaggacgct | 240 |
| gtccgatgct gacagaaagg gaggcaacag cagcgtgaag ttggaggctg gcctggccaa | 300 |
| caccatcacc agctttattg acaaagggca agatgaccga gtcccgtgg tcaggaagca | 360 |
| gaggtacgtg tttgacatta gtgccctgga aaggatgggc ctgctggggg ccgagctgcg | 420 |
| gatcttgcgg aagaagccct cggacacggc caagccagcg gccccggag gcgggcgggc | 480 |
| tgcccagctg aagctgtcca gctgccccag cggccggcag ccggcctcct tgctggatgt | 540 |
| gcgctccgtg ccaggcctgg acggatctgg ctgggaggtg ttcgacatct ggaagctctt | 600 |
| ccgaaacttt aagaactcgg cccagctgtg cctggagctg gaggcctggg aacggggcag | 660 |
| ggccgtggac ctccgtggcc tgggcttcga ccgcgccgcc cggcaggtcc acgagaaggc | 720 |
| cctgttcctg gtgtttggcc gcaccaagaa acgggacctg ttctttaatg agattaaggc | 780 |
| ccgctctggc caggacgata gaccgtgta tgagtacctg ttcagccagc ggcgaaaacg | 840 |
| gcgggcccca ctggccactc gccagggcaa gcgacccagc aagaacctta aggctcgctg | 900 |
| cagtcggaag gcactgcatg tcaacttcaa ggacatgggc tgggacgact ggatcatcgc | 960 |
| accccttgag tacgaggctt ccactgcga ggggctgtgc gagttcccat gcgctcccca | 1020 |
| cctggagccc acgaatcatg cagtcatcca gaccctgatg aactccatgg accccgagtc | 1080 |
| cacaccaccc acctgctgtg tgcccacgcg gctgagtccc atcagcatcc tcttcattga | 1140 |
| ctctgccaac aacgtggtgt ataagcagta tgaggacatg gtcgtggagt cgtgtggctg | 1200 |
| caggtag | 1207 |

<210> SEQ ID NO 2
<211> LENGTH: 2272
<212> TYPE: DNA
<213> ORGANISM: Homo sapiens

<400> SEQUENCE: 2

| | | |
|---|---|---|
| caaggagcca tgccagctgg acacacactt cttccagggc ctctggcagc caggacagag | 60 |
| ttgagaccac agctgttgag accctgagcc ctgagtctgt attgctcaag aagggccttc | 120 |
| cccagcaatg acctcctcat tgcttctggc cttttctcctc ctggctccaa ccacagtggc | 180 |
| cactcccaga gctggcggtc agtgtccagc atgtgggggg cccaccttgg aactggagag | 240 |
| ccagcgggag ctgcttcttg atctggccaa agaagcatc ttggacaagc tgcacctcac | 300 |
| ccagcgccca acactgaacc gccctgtgtc cagagctgct tgaggactg cactgcagca | 360 |
| cctccacggg gtcccacagg gggcacttct agaggacaac agggaacagg aatgtgaaat | 420 |
| catcagcttt gctgagacag gcctctccac catcaaccag actcgtcttg attttcactt | 480 |
| ctcctctgat agaactgctg gtgacaggga ggtccagcag gccagtctca tgttctttgt | 540 |
| gcagctccct tccaatacca cttggaccct gaaagtgaga gtccttgtgc tgggtccaca | 600 |
| taataccaac ctcaccttgg ctactcagta cctgctggag gtggatgcca gtggctggca | 660 |
| tcaactcccc ctagggcctg aagctcaagc tgcctgcagc caggggcacc tgaccctgga | 720 |
| gctggtactt gaaggccagg tagcccagag ctcagtcatc ctgggtggag ctgcccatag | 780 |
| gccttttgtg gcagcccggg tgagagttgg gggcaaacac cagattcacc gacgaggcat | 840 |
| cgactgccaa ggagggtcca ggatgtgctg tcgacaagag ttttttgtgg acttccgtga | 900 |
| gattggctgg cacgactgga tcatccagcc tgagggctac gccatgaact tctgcatagg | 960 |
| gcagtgccca ctacacatag caggcatgcc tggtattgct gcctcctttc acactgcagt | 1020 |

```
gctcaatctt ctcaaggcca acacagctgc aggcaccact ggaggggggct catgctgtgt    1080 acccacggcc cggcgccccc tgtctctgct ctattatgac agggacagca acattgtcaa    1140
gactgacata cctgacatgg tagtagaggc ctgtgggtgc agttagtcta tgtgtggtat    1200
gggcagccca aggttgcatg ggaaaacacg cccctacaga agtgcacttc cttgagagga    1260
gggaatgacc tcattctctg tccagaatgt ggactccctc ttcctgagca tcttatggaa    1320
attaccccac ctttgacttg aagaaacctt catctaaagc aagtcactgt gccatcttcc    1380
tgaccactac cctctttcct agggcatagt ccatcccgct agtccatccc gctagcccca    1440
ctccagggac tcagacccat ctccaaccat gagcaatgcc atctggttcc caggcaaaga    1500
cacccttagc tcacctttaa tagaccccat aacccactat gccttcctgt cctttctact    1560
caatggtccc cactccaaga tgagttgaca caaccccttc ccccaatttt tgtggatctc    1620
cagagaggcc cttctttgga ttcaccaaag tttagatcac tgctgcccaa aatagaggct    1680
tacctacccc cctctttgtt gtgagcccct gtccttctta gttgtccagg tgaactacta    1740
aagctctctt tgcatacctt catccatttt ttgtccttct ctgcctttct ctatgccctt    1800
aaggggtgac ttgcctgagc tctatcacct gagctcccct gccctctggc ttcctgctga    1860
ggtcagggca tttcttatcc ctgttccctc tctgtctagg tgtcatggtt ctgtgtaact    1920
gtggctattc tgtgtcccta cactacctgg ctacccccctt ccatggcccc agctctgcct    1980
acattctgat ttttttttt tttttttttt tgaaagtta aaaattcctt aatttttat    2040 tcctggtacc actaccacaa tttacagggc aatatacctg atgtaatgaa aagaaaaaga    2100
aaaagacaaa gctacaacag ataaaagacc tcaggaatgt acatctaatt gacactacat    2160
tgcattaatc aatagctgca cttttttgcaa actgtggcta tgacagtcct gaacaagaag    2220
ggtttcctgt ttaagctgca gtaacttttc tgactatgga tcatcgttcc tt           2272
```

<210> SEQ ID NO 3
<211> LENGTH: 401
<212> TYPE: PRT
<213> ORGANISM: Homo sapiens

<400> SEQUENCE: 3

```
Pro Gly Gly Pro Glu Pro Lys Pro Gly His Pro Pro Gln Thr Arg Gln
1               5                   10                  15

Ala Thr Ala Arg Thr Val Thr Pro Lys Gly Gln Leu Pro Gly Gly Lys
            20                  25                  30

Ala Pro Pro Lys Ala Gly Ser Val Pro Ser Ser Phe Leu Leu Lys Lys
        35                  40                  45

Ala Arg Glu Pro Gly Pro Pro Arg Glu Pro Lys Glu Pro Phe Arg Pro
    50                  55                  60

Pro Pro Ile Thr Pro His Glu Tyr Met Leu Ser Leu Tyr Arg Thr Leu
65                  70                  75                  80

Ser Asp Ala Asp Arg Lys Gly Gly Asn Ser Ser Val Lys Leu Glu Ala
                85                  90                  95

Gly Leu Ala Asn Thr Ile Thr Ser Phe Ile Asp Lys Gly Gln Asp Asp
            100                 105                 110

Arg Gly Pro Val Val Arg Lys Gln Arg Tyr Val Phe Asp Ile Ser Ala
        115                 120                 125

Leu Glu Lys Asp Gly Leu Leu Gly Ala Glu Leu Arg Ile Leu Arg Lys
    130                 135                 140

Lys Pro Ser Asp Thr Ala Lys Pro Ala Ala Pro Gly Gly Gly Arg Ala
145                 150                 155                 160
```

-continued

Ala Gln Leu Lys Leu Ser Ser Cys Pro Ser Gly Arg Gln Pro Ala Ser
            165                 170                 175

Leu Leu Asp Val Arg Ser Val Pro Gly Leu Asp Gly Ser Gly Trp Glu
            180                 185                 190

Val Phe Asp Ile Trp Lys Leu Phe Arg Asn Phe Lys Asn Ser Ala Gln
            195                 200                 205

Leu Cys Leu Glu Leu Glu Ala Trp Glu Arg Gly Arg Ala Val Asp Leu
        210                 215                 220

Arg Gly Leu Gly Phe Asp Arg Ala Arg Gln Val His Glu Lys Ala
225                 230                 235                 240

Leu Phe Leu Val Phe Gly Arg Thr Lys Arg Asp Leu Phe Phe Asn
            245                 250                 255

Glu Ile Lys Ala Arg Ser Gly Gln Asp Asp Lys Thr Val Tyr Glu Tyr
            260                 265                 270

Leu Phe Ser Gln Arg Arg Lys Arg Arg Ala Pro Leu Ala Thr Arg Gln
        275                 280                 285

Gly Lys Arg Pro Ser Lys Asn Leu Lys Ala Arg Cys Ser Arg Lys Ala
290                 295                 300

Leu His Val Asn Phe Lys Asp Met Gly Trp Asp Asp Trp Ile Ile Ala
305                 310                 315                 320

Pro Leu Glu Tyr Glu Ala Phe His Cys Glu Gly Leu Cys Glu Phe Pro
            325                 330                 335

Leu Arg Ser His Leu Glu Pro Thr Asn His Ala Val Ile Gln Thr Leu
        340                 345                 350

Met Asn Ser Met Asp Pro Glu Ser Thr Pro Pro Thr Cys Cys Val Pro
            355                 360                 365

Thr Arg Leu Ser Pro Ile Ser Ile Leu Phe Ile Asp Ser Ala Asn Asn
        370                 375                 380

Val Val Tyr Lys Gln Tyr Glu Asp Met Val Val Glu Ser Cys Gly Cys
385                 390                 395                 400

Arg

<210> SEQ ID NO 4
<211> LENGTH: 352
<212> TYPE: PRT
<213> ORGANISM: Homo sapiens

<400> SEQUENCE: 4

Met Thr Ser Ser Leu Leu Ala Phe Leu Leu Ala Pro Thr Thr
1               5                   10                  15

Val Ala Thr Pro Arg Ala Gly Gly Gln Cys Pro Ala Cys Gly Gly Pro
            20                  25                  30

Thr Leu Glu Leu Glu Ser Gln Arg Glu Leu Leu Leu Asp Leu Ala Lys
        35                  40                  45

Arg Ser Ile Leu Asp Lys Leu His Leu Thr Gln Arg Pro Thr Leu Asn
    50                  55                  60

Arg Pro Val Ser Arg Ala Ala Leu Arg Thr Ala Leu Gln His Leu His
65                  70                  75                  80

Gly Val Pro Gln Gly Ala Leu Leu Glu Asp Asn Arg Glu Gln Glu Cys
            85                  90                  95

Glu Ile Ile Ser Phe Ala Glu Thr Gly Leu Ser Thr Ile Asn Gln Thr
        100                 105                 110

Arg Leu Asp Phe His Phe Ser Ser Asp Arg Thr Ala Gly Asp Arg Glu
    115                 120                 125

Val Gln Gln Ala Ser Leu Met Phe Phe Val Gln Leu Pro Ser Asn Thr
         130                 135                 140

Thr Trp Thr Leu Lys Val Arg Val Leu Val Leu Gly Pro His Asn Thr
145                 150                 155                 160

Asn Leu Thr Leu Ala Thr Gln Tyr Leu Leu Glu Val Asp Ala Ser Gly
                165                 170                 175

Trp His Gln Leu Pro Leu Gly Pro Glu Ala Gln Ala Ala Cys Ser Gln
            180                 185                 190

Gly His Leu Thr Leu Glu Leu Val Leu Glu Gly Gln Val Ala Gln Ser
        195                 200                 205

Ser Val Ile Leu Gly Gly Ala Ala His Arg Pro Phe Val Ala Ala Arg
    210                 215                 220

Val Arg Val Gly Gly Lys His Gln Ile His Arg Arg Gly Ile Asp Cys
225                 230                 235                 240

Gln Gly Gly Ser Arg Met Cys Cys Arg Gln Glu Phe Phe Val Asp Phe
                245                 250                 255

Arg Glu Ile Gly Trp His Asp Trp Ile Ile Gln Pro Glu Gly Tyr Ala
            260                 265                 270

Met Asn Phe Cys Ile Gly Gln Cys Pro Leu His Ile Ala Gly Met Pro
        275                 280                 285

Gly Ile Ala Ala Ser Phe His Thr Ala Val Leu Asn Leu Leu Lys Ala
    290                 295                 300

Asn Thr Ala Ala Gly Thr Thr Gly Gly Gly Ser Cys Cys Val Pro Thr
305                 310                 315                 320

Ala Arg Arg Pro Leu Ser Leu Leu Tyr Tyr Asp Arg Asp Ser Asn Ile
                325                 330                 335

Val Lys Thr Asp Ile Pro Asp Met Val Val Glu Ala Cys Gly Cys Ser
            340                 345                 350

<210> SEQ ID NO 5
<211> LENGTH: 265
<212> TYPE: DNA
<213> ORGANISM: Homo sapiens

<400> SEQUENCE: 5
catccagcct gagggctacg ccatgaactt ctgcataggg cagtgcccac tacacatagc    60
aggcatgcct ggtattgctg cctcctttca cactgcagtg ctcaatcttc tcaaggccaa   120
cacagctgca ggcaccactg gagggggctc atgctgtgta cccacggccc ggcgcccct    180 gtctctgctc tattatgaca gggacagcaa cattgtcaag actgacatac ctgacatggt   240
agtagaggcc tgtgggtgca gttag                                         265

<210> SEQ ID NO 6
<211> LENGTH: 139
<212> TYPE: DNA
<213> ORGANISM: Homo sapiens

<400> SEQUENCE: 6
catcgcaccc cttgagtacg aggctttcca ctgcgagggg ctgtgcgagt tcccattgcg    60 ctccccacctg gagcccacga atcatgcagt catccagacc tgatgaact ccatggaccc   120 cgagtccaca ccacccacc                                                139

<210> SEQ ID NO 7
<211> LENGTH: 27
<212> TYPE: DNA

```
<213> ORGANISM: Homo sapiens

<400> SEQUENCE: 7
atgaactcca tggaccccga gtccaca                                          27

<210> SEQ ID NO 8
<211> LENGTH: 30
<212> TYPE: DNA
<213> ORGANISM: Homo sapiens

<400> SEQUENCE: 8
cttctcaagg ccaacacagc tgcaggcacc                                       30

<210> SEQ ID NO 9
<211> LENGTH: 9
<212> TYPE: PRT
<213> ORGANISM: Homo sapiens

<400> SEQUENCE: 9

Met Asn Ser Met Asp Pro Glu Ser Thr
1               5

<210> SEQ ID NO 10
<211> LENGTH: 10
<212> TYPE: PRT
<213> ORGANISM: Homo sapiens

<400> SEQUENCE: 10

Leu Leu Lys Ala Asn Thr Ala Ala Gly Thr
1               5                   10

<210> SEQ ID NO 11
<211> LENGTH: 44
<212> TYPE: DNA
<213> ORGANISM: artificial sequence
<220> FEATURE:
<223> OTHER INFORMATION: oligodT (16 residues) linked to adapter primer

<400> SEQUENCE: 11
agaattcgca tgccatggtc gacgaagctt ttttttttttt tttt                      44

<210> SEQ ID NO 12
<211> LENGTH: 24
<212> TYPE: DNA
<213> ORGANISM: artificial sequence
<220> FEATURE:
<223> OTHER INFORMATION: adaptor primer

<400> SEQUENCE: 12
agaattcgca tgccatggtc gacg                                             24

<210> SEQ ID NO 13
<211> LENGTH: 24
<212> TYPE: DNA
<213> ORGANISM: Homo sapiens

<400> SEQUENCE: 13
ggctacgcca tgaacttctg cata                                             24

<210> SEQ ID NO 14
<211> LENGTH: 24
<212> TYPE: DNA
<213> ORGANISM: Homo sapiens

<400> SEQUENCE: 14
```

```
acatagcagg catgcctggt attg                                          24

<210> SEQ ID NO 15
<211> LENGTH: 23
<212> TYPE: DNA
<213> ORGANISM: Homo sapiens

<400> SEQUENCE: 15
cttgagtacg aggctttcca ctg                                           23

<210> SEQ ID NO 16
<211> LENGTH: 24
<212> TYPE: DNA
<213> ORGANISM: artificial sequence
<220> FEATURE:
<223> OTHER INFORMATION: nested adaptor primer

<400> SEQUENCE: 16
attcgcatgc catggtcgac gaag                                          24

<210> SEQ ID NO 17
<211> LENGTH: 23
<212> TYPE: DNA
<213> ORGANISM: Homo sapiens

<400> SEQUENCE: 17
ggagcccacg aatcatgcag tca                                           23

<210> SEQ ID NO 18
<211> LENGTH: 23
<212> TYPE: DNA
<213> ORGANISM: Homo sapiens

<400> SEQUENCE: 18
acagcaggtg ggtggtgtgg act                                           23

<210> SEQ ID NO 19
<211> LENGTH: 20
<212> TYPE: DNA
<213> ORGANISM: Homo sapiens

<400> SEQUENCE: 19
ccagcagccc atccttctcc                                               20

<210> SEQ ID NO 20
<211> LENGTH: 24
<212> TYPE: DNA
<213> ORGANISM: Homo sapiens

<400> SEQUENCE: 20
tccagggcac taatgtcaaa cacg                                          24

<210> SEQ ID NO 21
<211> LENGTH: 24
<212> TYPE: DNA
<213> ORGANISM: Homo sapiens

<400> SEQUENCE: 21
actaatgtca aacacgtacc tctg                                          24

<210> SEQ ID NO 22
<211> LENGTH: 102
<212> TYPE: PRT
```

<213> ORGANISM: Homo sapiens

<400> SEQUENCE: 22

Cys Ser Arg Lys Ala Leu His Val Asn Phe Lys Asp Met Gly Trp Asp
1               5                   10                  15

Asp Trp Ile Ile Ala Pro Leu Glu Tyr Glu Ala Phe His Cys Glu Gly
            20                  25                  30

Leu Cys Glu Phe Pro Leu Arg Ser His Leu Glu Pro Thr Asn His Ala
        35                  40                  45

Val Ile Gln Thr Leu Met Asn Ser Met Asp Pro Glu Ser Thr Pro Pro
    50                  55                  60

Thr Cys Cys Val Pro Thr Arg Leu Ser Pro Ile Ser Ile Leu Phe Ile
65                  70                  75                  80

Asp Ser Ala Asn Asn Val Val Tyr Lys Gln Tyr Glu Asp Met Val Val
                85                  90                  95

Glu Ser Cys Gly Cys Arg
            100

<210> SEQ ID NO 23
<211> LENGTH: 101
<212> TYPE: PRT
<213> ORGANISM: Homo sapiens

<400> SEQUENCE: 23

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
    50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

<210> SEQ ID NO 24
<211> LENGTH: 101
<212> TYPE: PRT
<213> ORGANISM: Homo sapiens

<400> SEQUENCE: 24

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ser Ile Pro Lys Ala
    50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

```
Gly Cys Gly Cys Arg
            100

<210> SEQ ID NO 25
<211> LENGTH: 102
<212> TYPE: PRT
<213> ORGANISM: Homo sapiens

<400> SEQUENCE: 25

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Phe Pro Asp His Val Pro Lys
    50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
            100

<210> SEQ ID NO 26
<211> LENGTH: 102
<212> TYPE: PRT
<213> ORGANISM: Homo sapiens

<400> SEQUENCE: 26

Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100

<210> SEQ ID NO 27
<211> LENGTH: 102
<212> TYPE: PRT
<213> ORGANISM: Homo sapiens

<400> SEQUENCE: 27

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
            20                  25                  30

Glu Cys Ala Phe Pro Leu Asn Ser Tyr Met Asn Ala Thr Asn His Ala
        35                  40                  45
```

Ile Val Gln Thr Leu Val His Phe Ile Asn Pro Glu Thr Val Pro Lys
       50                      55                      60

Pro Cys Cys Ala Pro Thr Gln Leu Asn Ala Ile Ser Val Leu Tyr Phe
 65                  70                      75                  80

Asp Asp Ser Ser Asn Val Ile Leu Lys Lys Tyr Arg Asn Met Val Val
                 85                      90                      95

Arg Ala Cys Gly Cys His
            100

<210> SEQ ID NO 28
<211> LENGTH: 106
<212> TYPE: PRT
<213> ORGANISM: Homo sapiens

<400> SEQUENCE: 28

Cys Cys Arg Gln Glu Phe Phe Val Asp Phe Arg Glu Ile Gly Trp His
 1               5                      10                      15

Asp Trp Ile Ile Gln Pro Glu Gly Tyr Ala Met Asn Phe Cys Ile Gly
             20                      25                      30

Gln Cys Pro Leu His Ile Ala Gly Met Pro Gly Ile Ala Ala Ser Phe
             35                      40                      45

His Thr Ala Val Leu Asn Leu Leu Lys Ala Asn Thr Ala Ala Gly Thr
     50                      55                      60

Thr Gly Gly Gly Ser Cys Cys Val Pro Thr Ala Arg Arg Pro Leu Ser
 65                  70                      75                  80

Leu Leu Tyr Tyr Asp Arg Asp Ser Asn Ile Val Lys Thr Asp Ile Pro
                 85                      90                      95

Asp Met Val Val Glu Ala Cys Gly Cys Ser
            100                 105

<210> SEQ ID NO 29
<211> LENGTH: 106
<212> TYPE: PRT
<213> ORGANISM: Homo sapiens

<400> SEQUENCE: 29

Cys Cys Lys Lys Gln Phe Phe Val Ser Phe Lys Asp Ile Gly Trp Asn
 1               5                      10                      15

Asp Trp Ile Ile Ala Pro Ser Gly Tyr His Ala Asn Tyr Cys Glu Gly
             20                      25                      30

Glu Cys Pro Ser His Ile Ala Gly Thr Ser Gly Ser Ser Leu Ser Phe
             35                      40                      45

His Ser Thr Val Ile Asn His Tyr Arg Met Arg Gly His Ser Pro Phe
     50                      55                      60

Ala Asn Leu Lys Ser Cys Cys Val Pro Thr Lys Leu Arg Pro Met Ser
 65                  70                      75                  80

Met Leu Tyr Tyr Asp Asp Gly Gln Asn Ile Ile Lys Lys Asp Ile Gln
                 85                      90                      95

Asn Met Ile Val Glu Glu Cys Gly Cys Ser
            100                 105

<210> SEQ ID NO 30
<211> LENGTH: 105
<212> TYPE: PRT
<213> ORGANISM: Homo sapiens

<400> SEQUENCE: 30

Cys Cys Arg Gln Gln Phe Phe Ile Asp Phe Arg Leu Ile Gly Trp Asn

```
                1               5                  10                 15
Asp Trp Ile Ile Ala Pro Thr Gly Tyr Tyr Gly Asn Tyr Cys Glu Gly
                20                 25                 30

Ser Cys Pro Ala Tyr Leu Ala Gly Val Pro Gly Ser Ala Ser Ser Phe
                35                 40                 45

His Thr Ala Val Val Asn Gln Tyr Arg Met Arg Gly Leu Asn Pro Gly
                50                 55                 60

Thr Val Asn Ser Cys Cys Ile Pro Thr Lys Leu Ser Thr Met Ser Met
65                  70                 75                 80

Leu Tyr Phe Asp Asp Glu Tyr Asn Ile Val Lys Arg Asp Val Pro Asn
                85                 90                 95

Met Ile Val Glu Glu Cys Gly Cys Ala
                100                105

<210> SEQ ID NO 31
<211> LENGTH: 105
<212> TYPE: PRT
<213> ORGANISM: Homo sapiens

<400> SEQUENCE: 31

Cys His Arg Val Ala Leu Asn Ile Ser Phe Gln Glu Leu Gly Trp Glu
1               5                  10                 15

Arg Trp Ile Val Tyr Pro Pro Ser Phe Ile Phe His Tyr Cys His Gly
                20                 25                 30

Gly Cys Gly Leu His Ile Pro Pro Asn Leu Ser Leu Pro Val Pro Gly
                35                 40                 45

Ala Pro Pro Thr Pro Ala Gln Pro Tyr Ser Leu Leu Pro Gly Ala Gln
                50                 55                 60

Pro Cys Cys Ala Ala Leu Pro Gly Thr Met Arg Pro Leu His Val Arg
65                  70                 75                 80

Thr Thr Ser Asp Gly Gly Tyr Ser Phe Lys Tyr Glu Thr Val Pro Asn
                85                 90                 95

Leu Leu Thr Gln His Cys Ala Cys Ile
                100                105

<210> SEQ ID NO 32
<211> LENGTH: 36
<212> TYPE: DNA
<213> ORGANISM: artificial sequence
<220> FEATURE:
<223> OTHER INFORMATION: OD PCR amplification primer

<400> SEQUENCE: 32
atgaattccc atggacctgg gctggmakga mtggat                              36

<210> SEQ ID NO 33
<211> LENGTH: 22
<212> TYPE: DNA
<213> ORGANISM: Homo sapiens

<400> SEQUENCE: 33
acgtggggtg gaatgactgg at                                             22

<210> SEQ ID NO 34
<211> LENGTH: 22
<212> TYPE: DNA
<213> ORGANISM: Homo sapiens

<400> SEQUENCE: 34
```

-continued atattggctg gagtgaatgg at          22

<210> SEQ ID NO 35
<211> LENGTH: 22
<212> TYPE: DNA
<213> ORGANISM: Homo sapiens

<400> SEQUENCE: 35
atgtgggctg gaatgactgg at          22

<210> SEQ ID NO 36
<211> LENGTH: 22
<212> TYPE: DNA
<213> ORGANISM: Homo sapiens

<400> SEQUENCE: 36
acctgggctg gcaggactgg at          22

<210> SEQ ID NO 37
<211> LENGTH: 22
<212> TYPE: DNA
<213> ORGANISM: Homo sapiens

<400> SEQUENCE: 37
aggacctcgg ctggaagtgg at          22

<210> SEQ ID NO 38
<211> LENGTH: 22
<212> TYPE: DNA
<213> ORGANISM: Homo sapiens

<400> SEQUENCE: 38
gggatctagg gtggaaatgg at          22

<210> SEQ ID NO 39
<211> LENGTH: 22
<212> TYPE: DNA
<213> ORGANISM: Homo sapiens

<400> SEQUENCE: 39
aggatctggg ctggaagtgg gt          22

<210> SEQ ID NO 40
<211> LENGTH: 22
<212> TYPE: DNA
<213> ORGANISM: Homo sapiens

<400> SEQUENCE: 40
agctgggctg ggaacggtgg at          22

<210> SEQ ID NO 41
<211> LENGTH: 22
<212> TYPE: DNA
<213> ORGANISM: Homo sapiens

<400> SEQUENCE: 41
acatcggctg gaatgactgg at          22

<210> SEQ ID NO 42
<211> LENGTH: 22
<212> TYPE: DNA
<213> ORGANISM: Homo sapiens

<400> SEQUENCE: 42

```
tcatcggctg gaacgactgg at                                              22

<210> SEQ ID NO 43
<211> LENGTH: 29
<212> TYPE: DNA
<213> ORGANISM: artificial sequence
<220> FEATURE:
<223> OTHER INFORMATION: OID PCR amplification primer

<400> SEQUENCE: 43
atgaattcga gctgcgtsgg srcacagca                                       29

<210> SEQ ID NO 44
<211> LENGTH: 21
<212> TYPE: DNA
<213> ORGANISM: Homo sapiens
<220> FEATURE:
<223> OTHER INFORMATION: oligodT (16 residues) linked to adapter primer

<400> SEQUENCE: 44
gagttctgtc gggacacagc a                                               21

<210> SEQ ID NO 45
<211> LENGTH: 21
<212> TYPE: DNA
<213> ORGANISM: Homo sapiens

<400> SEQUENCE: 45
catcttttct ggtacacagc a                                               21

<210> SEQ ID NO 46
<211> LENGTH: 21
<212> TYPE: DNA
<213> ORGANISM: Homo sapiens

<400> SEQUENCE: 46
cagttcagtg ggcacacaac a                                               21

<210> SEQ ID NO 47
<211> LENGTH: 21
<212> TYPE: DNA
<213> ORGANISM: Homo sapiens

<400> SEQUENCE: 47
gagctgcgtg ggcgcacagc a                                               21

<210> SEQ ID NO 48
<211> LENGTH: 21
<212> TYPE: DNA
<213> ORGANISM: Homo sapiens

<400> SEQUENCE: 48
cagcgcctgc ggcacgcagc a                                               21

<210> SEQ ID NO 49
<211> LENGTH: 21
<212> TYPE: DNA
<213> ORGANISM: Homo sapiens

<400> SEQUENCE: 49
taaatcttgg gacacgcagc a                                               21

<210> SEQ ID NO 50
```

-continued

```
<211> LENGTH: 21
<212> TYPE: DNA
<213> ORGANISM: Homo sapiens

<400> SEQUENCE: 50
caggtcctgg ggcacgcagc a                                              21

<210> SEQ ID NO 51
<211> LENGTH: 21
<212> TYPE: DNA
<213> ORGANISM: Homo sapiens

<400> SEQUENCE: 51
ccctgggaga gcagcacagc a                                              21

<210> SEQ ID NO 52
<211> LENGTH: 21
<212> TYPE: DNA
<213> ORGANISM: Homo sapiens

<400> SEQUENCE: 52
cagcttggtg ggcacacagc a                                              21

<210> SEQ ID NO 53
<211> LENGTH: 21
<212> TYPE: DNA
<213> ORGANISM: Homo sapiens

<400> SEQUENCE: 53
cagcttggtg ggaatgcagc a                                              21
```